(12) United States Patent
Guan et al.

(10) Patent No.: US 8,540,416 B2
(45) Date of Patent: Sep. 24, 2013

(54) FLUIDIC FLOW MERGING APPARATUS

(75) Inventors: Xiaosheng Guan, Beijing (CN); Min Guo, Beijing (CN); Cheng Zhou, Beijing (CN); Yuming Hu, Beijing (CN); Jing Cheng, Beijing (CN)

(73) Assignees: Capitalbio Corporation, Beijing (CN); Tsinghua University, Beijing (CN)

( * ) Notice: Subject to any disclaimer, the term of this patent is extended or adjusted under 35 U.S.C. 154(b) by 1151 days.

(21) Appl. No.: 12/278,620

(22) PCT Filed: Feb. 6, 2007

(86) PCT No.: PCT/CN2007/000401
§ 371 (c)(1),
(2), (4) Date: Dec. 9, 2008

(87) PCT Pub. No.: WO2007/109956
PCT Pub. Date: Oct. 4, 2007

(65) Prior Publication Data
US 2010/0024888 A1     Feb. 4, 2010

(30) Foreign Application Priority Data

Mar. 27, 2006   (CN) .......................... 2006 1 0065951

(51) Int. Cl.
*G05D 7/00* (2006.01)
*B01F 5/04* (2006.01)
*F15C 3/00* (2006.01)

(52) U.S. Cl.
USPC ................... 366/172.1; 366/182.2; 422/503; 137/806

(58) Field of Classification Search
USPC .... 366/172.1, 182.2; 137/806; 422/503–504
See application file for complete search history.

(56) References Cited

U.S. PATENT DOCUMENTS

| 3,322,136 | A | * | 5/1967 | Matta .......................... 137/115.04 |
| 4,917,151 | A | * | 4/1990 | Blanchard et al. ............. 137/815 |
| 5,385,472 | A | * | 1/1995 | Mullin .......................... 434/126 |
| 6,591,852 | B1 | * | 7/2003 | McNeely et al. ............... 137/14 |
| 6,601,613 | B2 | | 8/2003 | McNeely et al. |
| 7,118,910 | B2 | * | 10/2006 | Unger et al. ................ 435/288.5 |
| 7,744,817 | B2 | * | 6/2010 | Bui ............................... 422/68.1 |
| 2002/0036018 | A1 | * | 3/2002 | McNeely et al. ............. 137/806 |
| 2002/0117772 | A1 | * | 8/2002 | Guillemette ................ 264/176.1 |
| 2004/0066703 | A1 | * | 4/2004 | Sparey-Taylor et al. ...... 366/127 |
| 2004/0228771 | A1 | * | 11/2004 | Zhou et al. .................... 422/102 |

(Continued)

FOREIGN PATENT DOCUMENTS

| CN | 1346053 | 4/2002 |
| CN | 1348100 | 5/2002 |
| WO | WO-98/52691 | 11/1998 |
| WO | WO-2004/043598 | 5/2004 |

OTHER PUBLICATIONS

International Search Report for PCT/CN2007/000401, mailed on May 8, 2007, 4 pages.

*Primary Examiner* — Joseph S Del Sole
*Assistant Examiner* — Nahida Sultana
(74) *Attorney, Agent, or Firm* — Morrison and Foerster LLP (57) ABSTRACT

The present invention provides a device for handling fluids, and more particularly a merging apparatus for fluidic and microfluidic devices utilizing passive valving in conjunction with a single sensor to uniformly blend contributory working fluid streams. Symmetric and non symmetric embodiments with and without branch channels are described. The present invention also provides methods for merging liquids using the device of the invention.

8 Claims, 12 Drawing Sheets

(56) References Cited

U.S. PATENT DOCUMENTS

| | | | |
|---|---|---|---|
| 2005/0129581 A1* | 6/2005 | McBride et al. | 422/100 |
| 2005/0252773 A1* | 11/2005 | McBride et al. | 204/450 |
| 2006/0165342 A1* | 7/2006 | Pau et al. | 385/12 |
| 2006/0254916 A1* | 11/2006 | Hernandez et al. | 204/453 |
| 2006/0275185 A1* | 12/2006 | Tonkovich et al. | 422/130 |
| 2007/0006926 A1* | 1/2007 | Prakash et al. | 137/800 |
| 2007/0119816 A1* | 5/2007 | Urquhart et al. | 216/84 |
| 2007/0280856 A1* | 12/2007 | Ulmanella et al. | 422/100 |
| 2009/0197977 A1* | 8/2009 | Haeberle et al. | 516/10 |
| 2009/0291435 A1* | 11/2009 | Unger et al. | 435/6 |
| 2010/0154890 A1* | 6/2010 | Maerkl et al. | 137/1 |
| 2010/0184202 A1* | 7/2010 | McBride et al. | 435/287.2 |
| 2011/0048543 A1* | 3/2011 | Prakash et al. | 137/2 |
| 2011/0053784 A1* | 3/2011 | Unger et al. | 506/7 |
| 2011/0114190 A1* | 5/2011 | Wen et al. | 137/1 |
| 2011/0189678 A1* | 8/2011 | McBride et al. | 435/6.12 |
| 2011/0310694 A1* | 12/2011 | Urquhart et al. | 366/132 |
| 2012/0136492 A1* | 5/2012 | Amin et al. | 700/285 |
| 2012/0285548 A1* | 11/2012 | Layman et al. | 137/13 |
| 2012/0315203 A1* | 12/2012 | Baroud et al. | 422/503 |

* cited by examiner

FLUIDIC FLOW MERGING APPARATUS

CROSS-REFERENCE TO RELATED APPLICATIONS

This application is the national phase of PCT application PCT/CN2007/000401 having an international filing date of Feb. 6, 2007, which claims priority from China application number 200610065951.2 filed Mar. 27, 2006. The contents of these documents are incorporated herein by this reference.

TECHNICAL FIELD

The present invention relates to fluid handling devices, and more particularly to flow merging apparatus for fluidic or microfluidic devices.

BACKGROUND ART

Figure 1A:
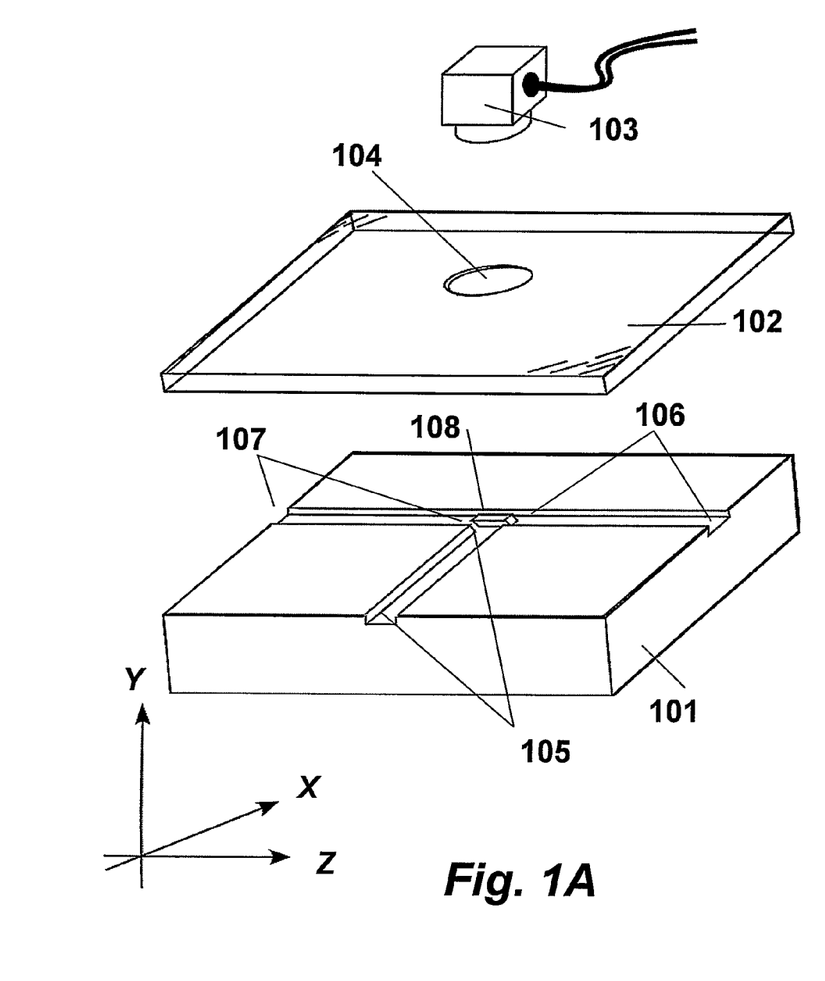
FIGS. 1A and 1B respectively provide exploded and assembled cross-sectional views according to a first embodiment of the invention.
Figure 1B:
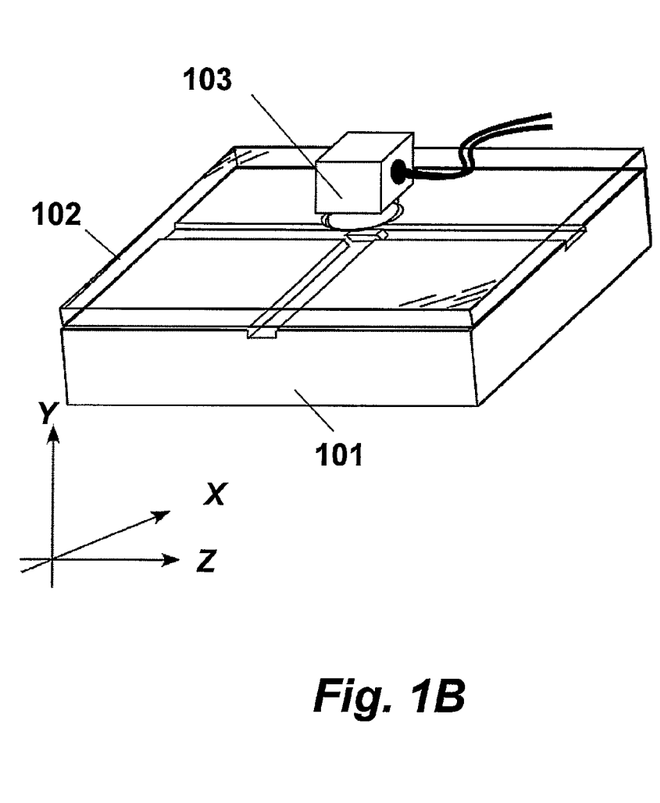

Fluidic devices can have integrated fluid channels for directing and controlling the transport of fluids. Microfluidics, a miniaturized form of fluidics, has emerged as a new approach for improving the performance and functionality of such systems for chemical and biochemical synthesis, as well as chemical, biochemical, and medical analysis. Miniaturization and new effects in micro-scale promise completely new system solutions in these fields. Dimension reduction results in faster processes with reduced reagent and sample consumption rates. The small size scale also encourages parallel processing, in which more compounds can be produced and/or analyzed simultaneously. Massively parallel processing can speed DNA, RNA, protein, immunologic, and other tests to reduce time intervals for drug discovery and medical diagnosis. Currently, microfluidic based microanalysis systems for such applications typically have fluid channel dimensions on the order of tenths of millimeters to several millimeters, although future trends are to further reduce channel dimensions. Various microfluidic components have also been demonstrated on the same size scale, for example: micro-valves, micro-pumps, micro-flow sensors, micro-filters, micro-mixers, micro-reactors, micro-separators, and micro-dispensers, to name just a few. The book, FUNDAMENTALS AND APPLICATIONS OF MICROFLUIDICS by Nam-Trung Nguyen and Steven T. Werely, published by Artech House of Boston, U.S.A., in 2002 provides an overview of some microfluidic technologies and applications. FIGS. 1A and 1B illustrated exploded and assembled perspective views of a fluidic or microfluidic device composed of a body component 101 to which a cover component 103 is affixed. Body component 101 contains channels 102 and other fluidic or microfluidic components formed therein.

In fluidic systems, and microfluidic systems in particular, it is often desirable to mix fluid streams prior to subsequent processing. Merging separate fluid streams in a uniform and reproducible manner in fluidic systems, and in particular in microfluidic systems can be difficult. Often, one fluid stream may reach the merging point earlier than another due to unmatched flow impedances or driving forces. Sometimes an air bubble can be trappedin the merged stream. This can be problematical if downstream operations require a homogeneous liquid media, free of entrapped bubbles. For example, if the downstream process is a DNA microarray hybridization, the presence of air bubbles could obstruct the binding of target molecules in a buffer with immobilized probes on the microarray.

U.S. Pat. No. 6,601,613, issued to McNeely et al. on Aug. 5, 2003 (hereinafter "McNeely"), teaches the use of passive valves formed in microfluidic channels by reducing channel width and/or height to help overcome the problem discussed above. The passive valves act as barriers to impede the flow of solution until enough force is built up to overcome the force the pressure barrier. Flow through multiple channels can be regulated to allow a series of sister wells or chambers to fill prior to the fluid flowing beyond. A hydrophobic vent structure is introduced to allow entrapped bubbles to escape subsequent to merging. For such mechanism to work well, the initially opened vent needs to be closed by the time it is passed by the fluid tails; otherwise, the vent could leak fluid in many operational situations. Therefore, in general the hydrophobic vent needs to be used in conjunction with a feedback control system comprising an active valve, as well as a sensor to open the active valve for bubble venting, but to keep the valve closed at other times. Another disadvantage is that additional steps are required during device fabrication in order to render the gas vent channel hydrophobic in substrates often made of hydrophilic materials such as polymethylmethacrylate (PMMA), polycarbonate (PC) or glass. An additional difficulty of this approach is that uniformly creating passive valves by reducing microfluidic channel width necessitates tighter dimensional tolerances for the microfluidic device, reducing yield and adding to fabrication cost.

SUMMARY OF EMBODIMENTS OF THE INVENTION

Embodiments of the present invention provide fluidic flow merging apparatuses that overcome the tight fabrication tolerance and leakage problems described above. The operational mechanisms employ passive valving, but do not require tighter dimensional tolerances, because microchannels remain the same size throughout the device. The need for bubble venting channels is obviated by preventing the formation of bubbles in a merged stream.

According to a first embodiment, a narrowing of microchannel dimensions is replaced by an effective narrowing of flow path, which is accomplished by forming an obstruction in the junction area instead of narrowing tributary microchannels. This localization of flow restriction to junction area means that a single flow sensor can be used to monitor the merging process, rather than individual flow sensors on all tributary and effluent paths. Therefore, a much simpler control scheme can be used with this approach.

According to the first embodiment, a fluidic flow merging apparatus comprises: first and second tributary channels; an effluent channel; a junction formed at the joining of the first and second tributary channels, and the effluent channel; a flow obstruction formed within the junction; and a fluid sensor configured proximate to the junction to sense the presence of working fluids.

A second embodiment is based on the fact that some passive valving forces are present at all channel junctions because of the discontinuity of at least one of the straight channel walls. This valving effect can be difficult to exploit because its magnitude is relatively small compared with that generated by either a narrowing of microchannel dimension or a narrowing of flow path, as mentioned earlier. However, if the fluid back pressure can be reduced to less than the valving capacity of the channel intersections, the channel intersections can be effective as passive valves. The second embodiment achieves this goal by a unique design of fluidic paths, as well as an associated merging scheme, without having to sacrifice fluid flow rates. Fluid back pressure is maintained at an operational level by providing tributary fluid flow through a double-merging fluidic path, so an unmodified channel junction can function effectively as a passive valve. One advantage is that this embodiment comprises microchannels of uniform cross-section. Another advantage is that a single sensor is adequate to trigger all needed control actions. Of course, the flow path narrowing obstruction described in connection with the first embodiment, can also be used with the second embodiment, if desired.

According to the second embodiment, a fluidic flow merging apparatus comprises: a first tributary channel; a branching channel, joined to the first tributary channel at a first junction; a second tributary channel; an intermediate effluent channel joined to the first tributary channel and the second tributary channel at a second junction; an effluent channel, joined to the intermediate effluent channel and the branching channel at a third junction; and a fluid sensor configured proximate to the second junction to sense the presence of working fluids. Some embodiments can further comprise a flow obstruction formed in the second junction.

A third embodiment of the invention is based on a symmetrical layout of the second embodiment of the invention. According to the third embodiment, a fluidic flow merging apparatus comprises: a first tributary channel; a first intermediate tributary channel; a first branching channel, joined to the first tributary channel and the first intermediate tributary channel at a first junction; a second tributary channel; a second intermediate tributary channel; a second branching channel, joined to the second tributary channel and the second intermediate tributary channel at a second junction; a third junction joining the first and second branching channels; an effluent channel; a fourth junction joining the first intermediate tributary channel, the second intermediate tributary channel, and the effluent channel; and a fluid sensor in each of the first and second branching channels, each sensor configured proximate to the third junction to sense the presence of working fluids. Further embodiments can also comprise a flow obstruction formed in the second junction.

In all of the embodiments, hydrophilic materials can be used to construct channel, junction, and obstruction walls.

For all of the embodiments, the fluidic flow merging apparatus can further comprise: a pressure pump configured to drive a working fluid flow in one of the tributary channels; and a controller configured to be in operable communication with the fluid sensor and the pressure pump; wherein the controller is configured to control the pressure pump responsive to a signal from the fluid sensor. In some of these embodiments, the controller can be configured to reduce a working fluid drive pressure from the pressure pump responsive to a first signal from the fluid sensor, and to restore the working fluid drive pressure responsive to a second signal from the fluid sensor.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

Figures one through ten are labeled with coordinate axes that cross reference orientations and views among the figures. When the text herein refers to "top," it refers to a drawing aspect presenting itself as viewed from the positive y-axis direction. When the text refers to "bottom," it refers to a drawing aspect presenting itself as viewed from the negative y-axis direction. Although the axes shown are in particular orientations in the drawings, the actual physical structures illustrated may be rotated to any particular orientation without performance impact, as long as component alignments are maintained and unless otherwise stated.

The figures provided are merely representational and may not be drawn to scale. Certain proportions thereof may be exaggerated, while others may be minimized. The figures are intended to illustrate various implementations of the invention that can be understood and appropriately carried out by those of ordinary skill in the art. Commonly designated elements among the various figures refer to common or equivalent elements in the depicted embodiments. The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF EMBODIMENTS OF THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this section prevails over the definition that is incorporated herein by reference.

As used herein, "a" or "an" means "at least one" or "one or more."

Embodiments of the flow merge apparatus can be made using techniques that are commonly used to make microfluidic devices and systems. Such techniques span a variety of diverse materials, fabrication, and assembly methods. Materials can be organic or inorganic, and be hydrophobic or hydrophilic to differing extents. A combination of different materials can be used in the same microfluidic device or system. Fabrication methods can be specific to specific types of materials, and can include photolithography; physical, wet, and dry-chemical etching; subtractive and additive material transfer; non-optical transfer printing; contact molding; injection molding; casting; micro-stereo lithography; and micro-machining. Assembly methods can include: anodic, direct, adhesive, and eutectic bonding; and press-fit. The selection of fabrication and assembly methods can affect the choice of microfluidic device and system design variations, or vice versa. This will be discussed below in connection with various embodiments of the wicking inhibitor.

As discussed above, various materials, fabrication methods, and assembly techniques can be used in the fabrication of microfluidic devices. The present discussion will focus on a subset of these in relation to embodiments of the current invention for the sake of focus and brevity, although further equivalent embodiments using other materials, fabrication methods, and assembly techniques would be apparent to one of ordinary skill in the art after reading the disclosure.

Inorganic materials include silicon, glasses, metals, and metal alloys. Glass is principally amorphous silicon dioxide ($SiO_2$) with varying amounts of additional elements in different types of glass. Among the desirable properties of glass for microfluidic device substrates are mechanical strength, dimensional stability, and low cost. A substrate of glass can form an active layer by having channels and other microfluidic structure formed in its surface, or it may merely serve as a mechanical support for active layers of other materials. Surface structures may be formed in glass by wet or dry chemical etching, mechanical ablation or milling, molding, and micromachining. Glass surfaces tend to be hydrophilic.

Typical polymer materials for other microfluidic device layers include thermosetting polymers such as polydimethylsiloxane (PDMS), as well as thermoplastic polymers such as: (i) polymethylmethacrylate (PMMA); (ii) polycarbonate (PC); (iii) polyoxymethylene (POM); and polyamide (PA).

PDMS has an inorganic siloxane backbone with organic methyl groups attached to the silicon. Both prepolymers and curing agents are commercially available. PMDS has a low interfacial free energy, which provides a relatively chemically unreactive, hydrophobic surface, although this can be modified with plasma treatment. PDMS is stable against temperature and humidity. PDMS is transparent, allowing for the visual examination of microfluidic structures and their operations. PDMS is flexible, so it can conform to nonplanar structures. PDMS is optically curable, so micro-stereo lithography can be used to form PDMS microfluidic structures, although PDMS structures can also be cast molded by applying a prepolymer solution to a mold, curing at an elevated temperature, and subsequently peeling the PMDS structure from the mold. The cast molding technique is capable of fabricating relief features down to the order of tens of microns across and deep, and is particularly low cost and does not require large capital investments in manufacturing equipment.

Structures can be formed in the thermoplastic polymers by using compression molding, injection molding, or micro-stereo lithography. Compression molding involves heating the polymer above its glass transition temperature and pressing it against a mold to form relief features, similar to the cast molding technique described in the previous paragraph. Injection molding involves heating the polymer above its glass transition temperature and pressure injecting it into a mold. After cooling, the mold is dismantled, and the molded part is removed.

All of the above fabrication techniques tend to create microfluidic layers with surface features formed in relief. Thus blind holes can be formed, but through holes can require further processing. Through holes (and other through structures) can be drilled by a variety of techniques, such as: (i) laser micro-machining using excimer, Nd:YAG, or $CO_2$ lasers; (ii) focused ion beam; (iii) micro-electric discharge; (iv) powder blasting; (v) ultrasonic micro-machining; or (vi) reduced-scale mechanical machining, all of which are well known to one of ordinary skill in the art.

Layers and substrate layers as discussed above can be assembled into microfluidic devices and systems using direct or adhesive bonding.

For direct bonding, the surfaces of layers to be bonded are cleaned and the layers are aligned relative to one another and pressed together to form a sandwiched structure. Thermoplastic polymers can be bonded together by heating to temperatures above their glass transition temperature. In cases of thermosetting polymers with low surface energy such as PMDS, layers can be bonded together under pressure at room temperature. PMDS layers can also bond to glass under similar conditions. Another method to bond layers together is wet bonding. In wet bonding, the surfaces to be bonded are wetted with a solvent, and then pressed together. Bonding is accomplished after evaporating the solvent.

Adhesive bonding uses an intermediate layer to glue layers together. Depending on substrate and layer materials, the intermediate adhesive layer can comprise epoxies, photoresists, or other polymers. The intermediate adhesive layer can be applied to a surface to be bonded, through a removable mask, in order to exclude adhesive from microfluidic structures, as necessary. Techniques for such selective application are well known to one of ordinary skill in the art. Some adhesive layers can be cured by ultraviolet light, while other adhesive layers can be chemically cured, or cured at elevated temperatures.

The embodiment presented here, will describe embodiments using a two layer structure, without loss of generality.

Figure 2:
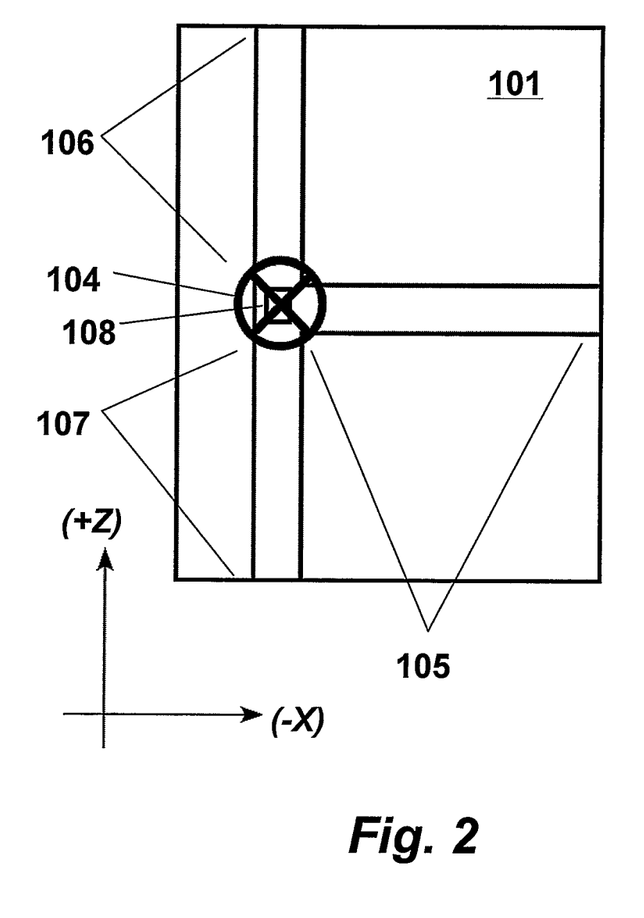
FIG. 2 provides a top view according to a first embodiment of the invention.
Figure 3A:
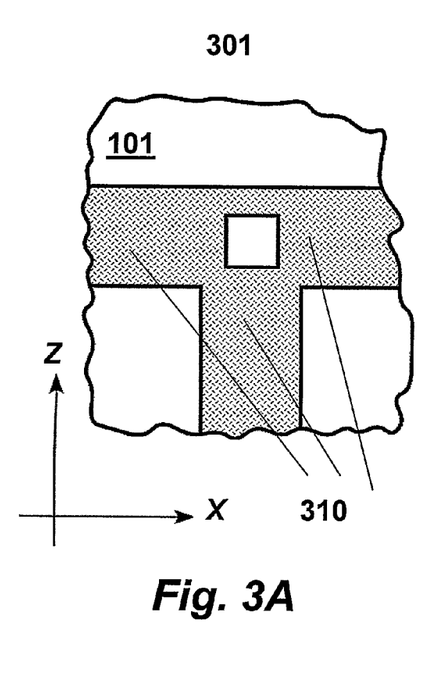
FIGS. 3A through 3C provide top views illustrating flow obstructions according to various embodiments of the invention.
Figure 3B:
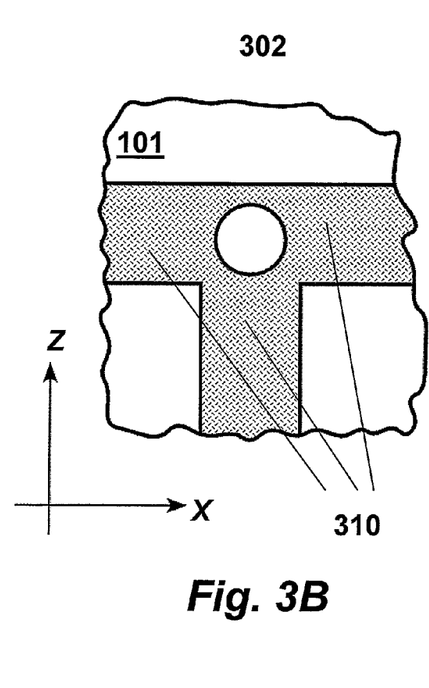
Figure 3C:
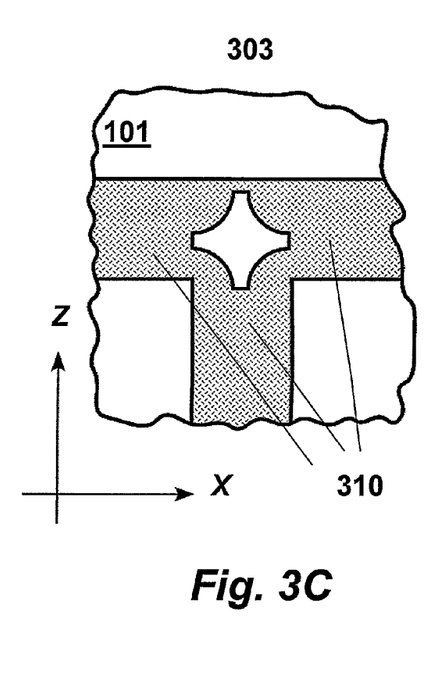

FIGS. 1A and 1B respectively provide exploded and assembled cross-sectional views according to a first embodiment of the invention. FIG. 2 provides a top view according to the first embodiment of the invention. Layer 101 has microfluidic channels 105, 106, and 107 formed therein, and converging at a junction in which flow obstruction 108 is formed. When assembled, cover layer 102 is bonded to the top of layer 101, thereby providing top walls for the microfluidic channels and junctions. Junction fluid sensor 103 is positioned proximate to the microfluidic channel junction area. Optional sensor positioning alignment recess 104 can help position sensor 104, especially in situations where cover layer 102 is not transparent. Sensor 103 can be of the optical (transmissive or reflective), capacitance, heat capacity (heater with coupled temperature sensor), or ultrasonic (transmissive or reflective) type that does not require contact with a working fluid. Alternatively, if sensor 104 is of the resistive type, fluid contact electrodes that penetrate cover layer 102 and/or layer 101 would be provided. Generally such sensors detect an attribute of a working fluid presence such as optical density, mass density, heat capacity, dielectric constant, resistivity, etc. and are able to sense the arrival of individual tributary fluid flow boundary fronts at a junction. Such types of sensors are well known in the art. FIGS. 3A through 3C provide top views illustrating flow obstructions according to various embodiments of the invention. Rectangular, circular, and indented structure are shown as a few examples.

Figure 4A:
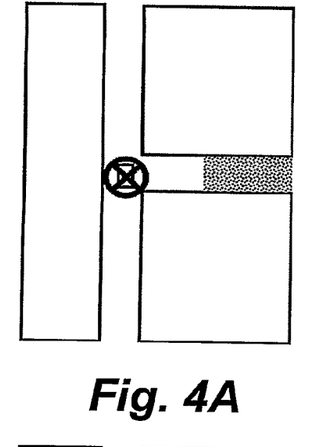
FIGS. 4A through 4G illustrate top views of an operation of the first embodiment of the invention.
Figure 4B:
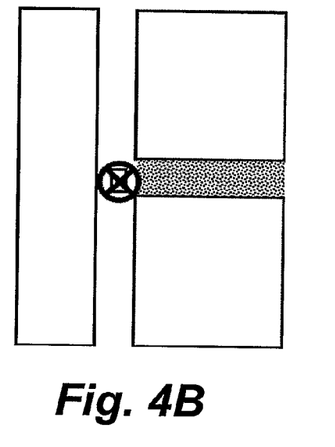
Figure 4C:
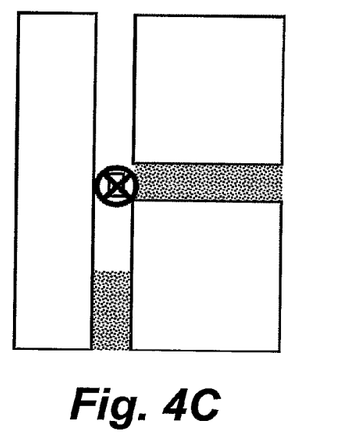
Figure 4D:
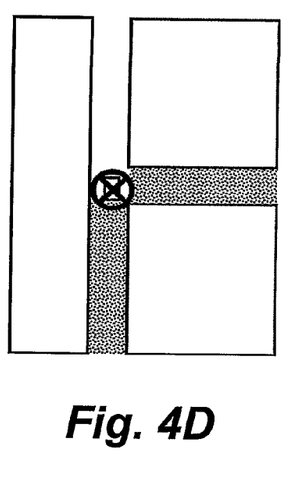
Figure 4E:
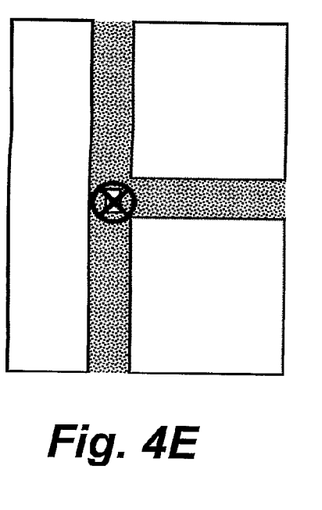

FIGS. 4A through 4G illustrate top views of an operation of the first embodiment of the invention. In FIG. 4A, a first working fluid is shown approaching the junction in a first of two working fluid tributary channels. The flow pressure of the first working fluid is low enough that fluid flow can be stopped at the junction obstruction. In FIG. 4B, the first working fluid reaches the junction, and the junction sensor detects the arrival of the first working fluid at the junction. At this point, the control system can reduce or stop the drive pressure of the first working fluid. FIG. 4C shows a second working fluid approaching the junction through a second tributary. FIG. 4D shows the second working fluid reaching the junction, which is also detected by the junction sensor. Responsive to junction sensor signals, the pressures driving the flow of the first and/or second working fluids can be increased by a control system to the point where they can overcome the passive valving effect of the junction and flow together in the effluent microchannel as shown in FIG. 4E.

Figure 4F:
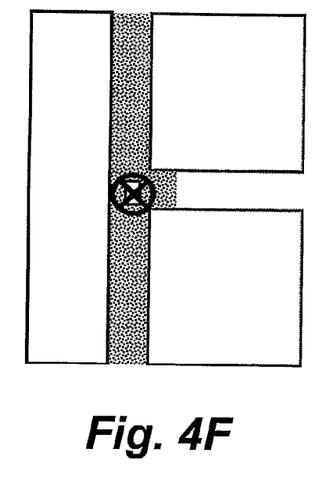

Considering FIG. 4E in more detail, the two working fluids flow side-by-side, forming a confluent downstream flow, as desired in some cases, and this scenario can be achieved by simultaneously driving the two fluids. However, it is not a trivial task to make the trailing boundaries of the two working fluids arrive at the junction at exactly the same time. FIG. 4F illustrates the case in which the trailing boundary of the first working fluid arrives at the junction first. (Alternately, the trailing boundary of the second working fluid could arrive at the junction first in other situations.) For some applications, a well-mixed downstream flow may be desired. For this purpose, one approach is to alternately drive the two working fluids in turn for a short period of time repetitively. For example, first drive the first fluid but shut off the second fluid for 2 seconds, then shut off the first fluid but drive the second fluid for 2 seconds, then repeat this process for many times. The interface between any two consecutive plugs of the fluids will be quickly distorted by parabolic velocity field that is characteristic for a channeled flow, resulting in a subsequently well mixed fluid stream. Clearly, in this latter situation, the trailing boundary of one working fluid is bound to come to the junction earlier than that of the other.

Figure 4G:
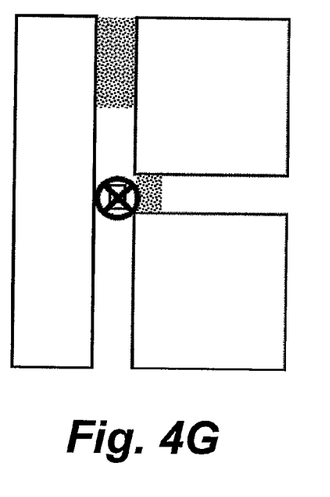

Therefore, the more general scenario is that one of the trailing boundaries arrives first at the junction as shown in FIG. 4F. The trailing boundary arrival can trigger a sensor signal so that the control system shuts off its driving force immediately, and let passive valving effect generated by the narrowed flow path to at least temporarily retain the trailing boundary at the junction. By doing so, the air entrained the trailing boundary will not be able to invade the junction to cause a downstream fluid discontinuity. The second fluid stream whose trailing boundary has not yet arrived at the junction can now be driven completely past the junction by overcoming the aforementioned passive valving effect that will be also experienced by the second fluid. In this manner, a continuous downstream flow, either confluent or well-mixed, can be created without fluid voids. FIG. 4F shows the trailing boundaries of the first working fluid approaching the junction. FIG. 4G shows the trailing boundary of merged working fluids as it departs from the junction.

Figure 5A:
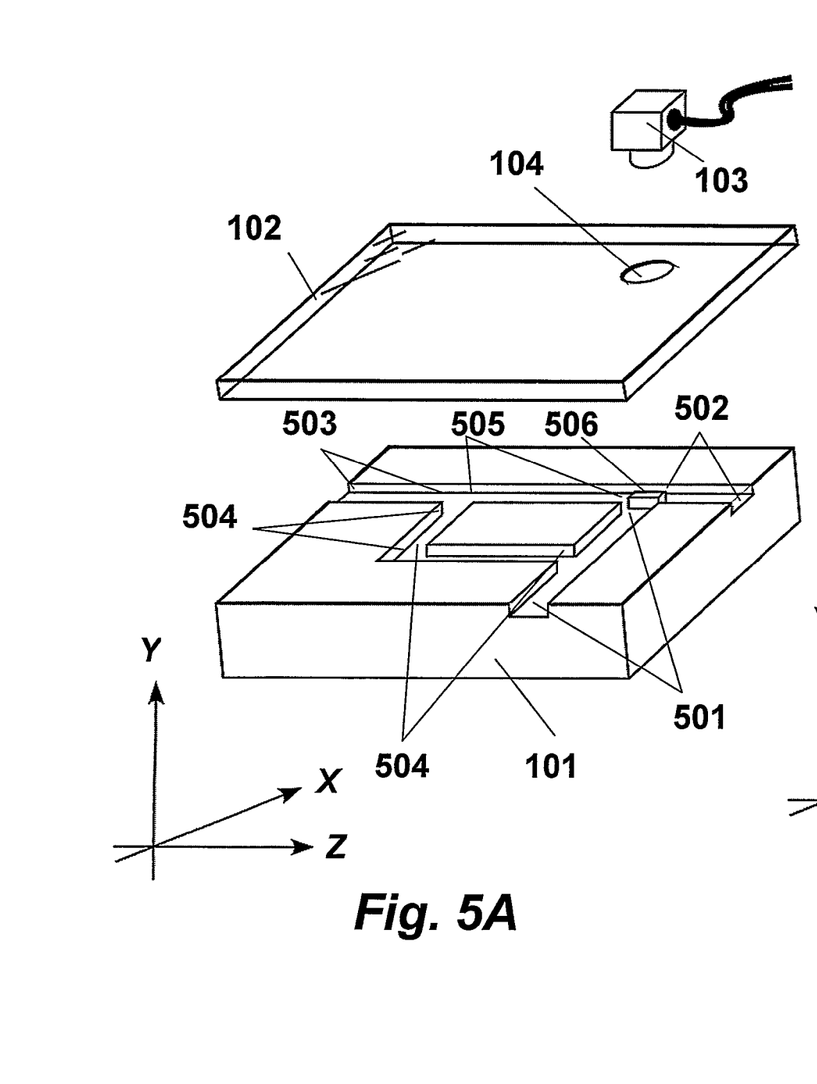
FIGS. 5A and 5B respectively provide exploded and assembled views according to a second embodiment of the invention.
Figure 5B:
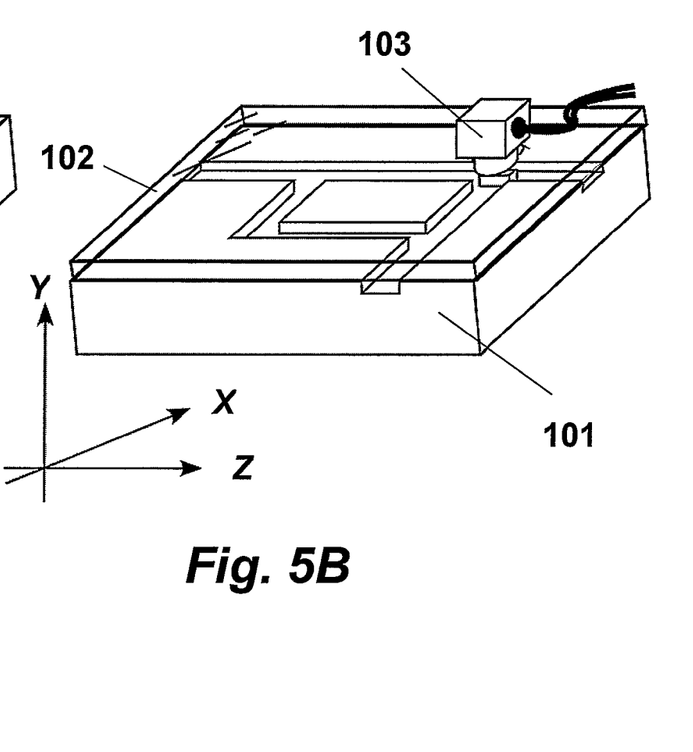
Figure 6:
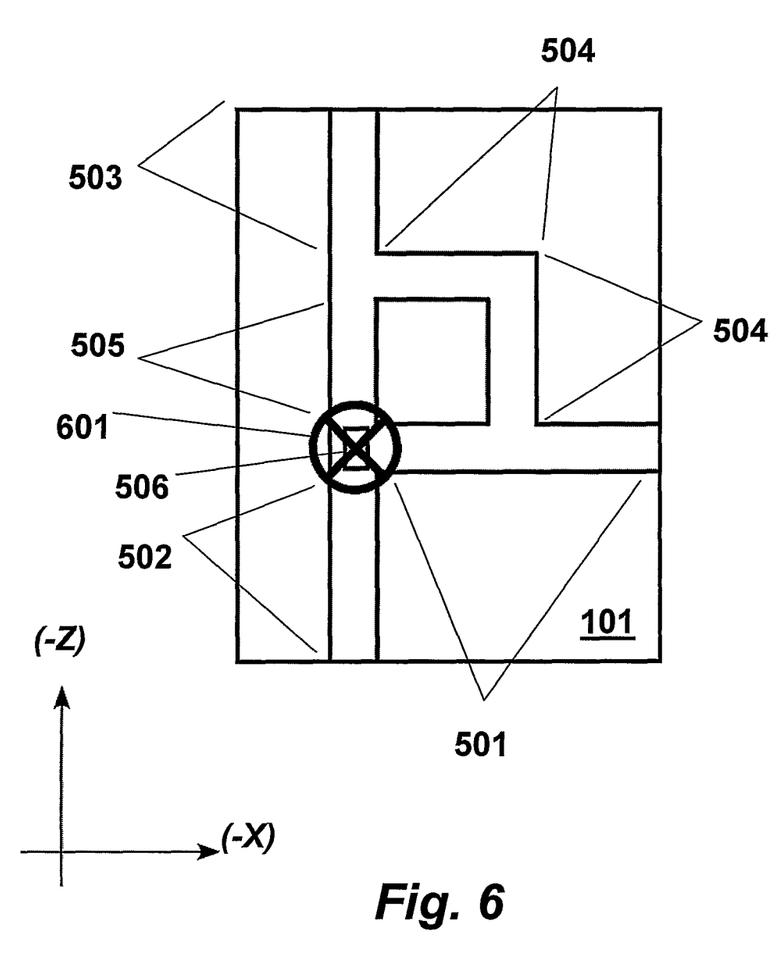
FIG. 6 provides a top view according to a second embodiment of the invention.

FIGS. 5A and 5B respectively provide exploded and assembled views according to a second embodiment of the invention. FIG. 6 provides a top view according to the second embodiment of the invention. First and second working fluids from first and second tributary channels 501 and 502 are to be merged. The first tributary channel 501 has side or branch channel 504 branching off of it at a first junction. According to this embodiment the flow obstruction 506 at a second junction between first and second tributary channels 501 and 502, and intermediate effluent channel 505 is optional. A third junction joins branch channel 504, intermediate effluent channel 505, and effluent channel 503. Junction sensor position 506 is noted on the drawing, proximate to the second junction.

Figure 7A:
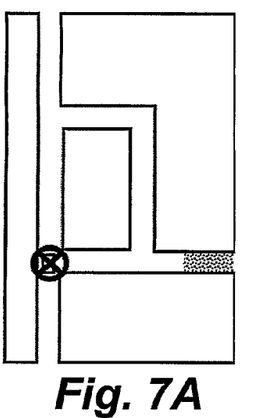
FIGS. 7A through 7I illustrate top views of an operation of the second embodiment of the invention.
Figure 7B:
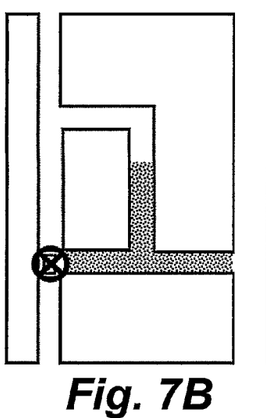
Figure 7C:
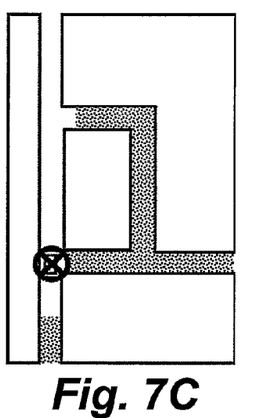
Figure 7D:
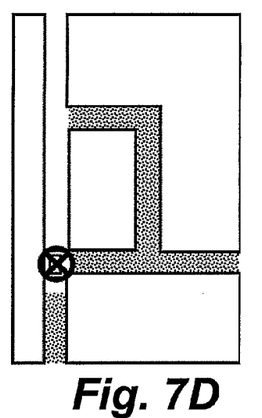
Figure 7E:
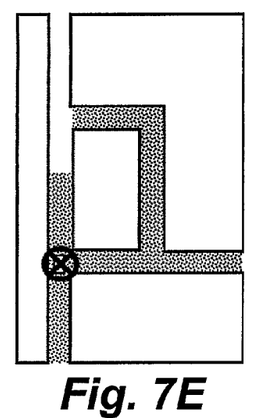
Figure 7F:
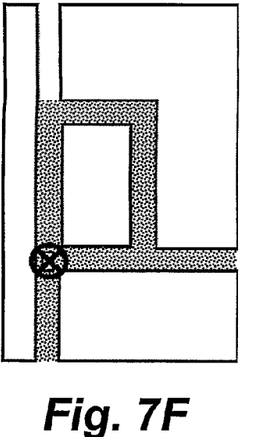
Figure 7G:
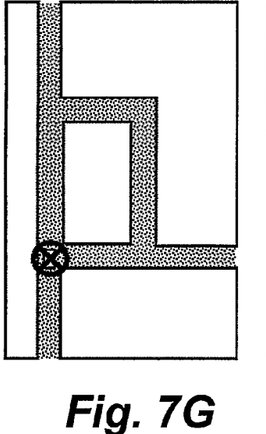

FIGS. 7A through 7I illustrate top views of an operation of the second embodiment of the invention. FIG. 7A shows the first working fluid approach the first junction where flow is split between channels 501 and 504. FIG. 7B shows the first working fluid flow stopping at the second junction, but continuing in side channel 504. The arrival of the first working fluid at the junction can be sensed by the junction sensor, and used to turn off the driving pressure of the first working fluid. The first working fluid flow tends to stop at the second junction because of the junction's passive valving effect as described above. Optionally, a fluid flow obstruction may be included to further increase the valving effect. FIG. 7C shows a second working fluid approaching the second working junction in the second tributary channel 502. FIG. 7D shows the second working fluid arriving at the junction, an event that is also detected by the junction sensor. The detection of the second working fluid's arrival can trigger the control system to resume the flow pressure for the first working fluid, so that the first and second working fluid streams are merged at the third junction as shown in FIGS. 7E through 7G. Regarding FIGS. 7E through 7G, we would like to emphasize the fact that in general the first and second fluid streams do not arrive at the third junction at the same time, however, because of the passive valving effect induced by the third junction, the first-arrived fluid stream will be temporarily stopped by the third junction, and wait for the other fluid stream to catch up, resulting in an automatic merge at the third junction.

Again referring to FIGS. 7E through 7G, it should be pointed out that both during and after the merge at the third junction, depending on pressure difference between the first and second junction, the first working fluid might well be partially advancing from the second to the third junction via channel 505, or the other way around, the second working fluid might well be partially advancing from the second to the third junction via channel 504. In other words, in most general cases, the channel 505 does not have to be flowing solely the second working fluid, and the channel 504 does not have to be flowing solely the first working fluid during and after the merge at the third junction.

Figure 7H:
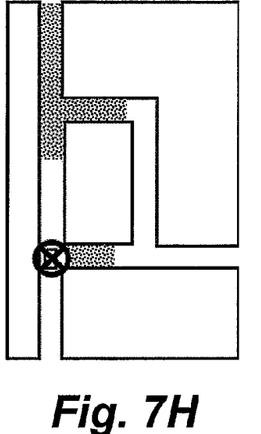
Figure 7I:
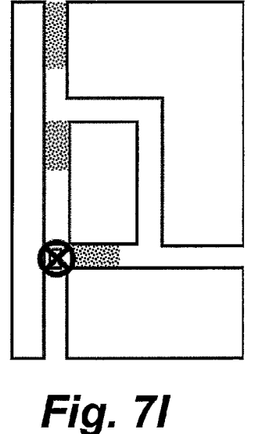

Corresponding to FIG. 7H and FIG. 7I, it is helpful to provide more details on how the control system deals with the trailing boundaries of the working fluids to ensure a continuous downstream flow, and how the small amount of residual fluids in the double merging structure is created. In fact, FIG. 7H shows that the trailing boundary of the second working fluid passes the sensor first, which triggers the control system to shut off immediately the driving force of the second working fluid.

Meanwhile, flowing of the first working fluid continues (or is resumed in case that the two working fluids have been driven in turn to obtain a well-mixed downstream flow, such has been discussed above. FIG. 7I shows that the first working fluid cannot be driven out of the second junction because of the passive valving effect induced by the second junction, and for this reason there is no flow in channel 505, which ensures that air within the channel 505 entailing the trailing boundary of the second working fluid not to be pushed past the third junction. The trailing boundary of the first working fluid is only able to subsequently pass the first junction, advance along the channel 504, and pass the third junction. Therefore, in the end, small amounts of residual working fluids are left within channel 505 and within the segment of the channel 501 between the first and second junction. The residual, unmixed working fluid can be subsequently flushed, prior to reuse of the device. In cases where the device is intended for one-time use, there is no need for flushing because the residual fluid does not affect downstream fluid handling.

Figure 8A:
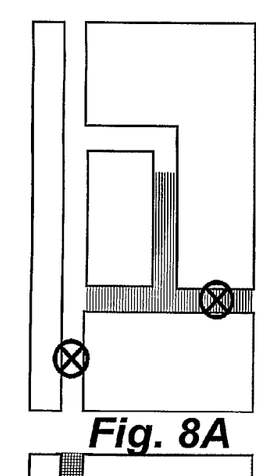
FIGS. 8A through 8G illustrate top views of an operation of a third embodiment of the invention.
Figure 8B:
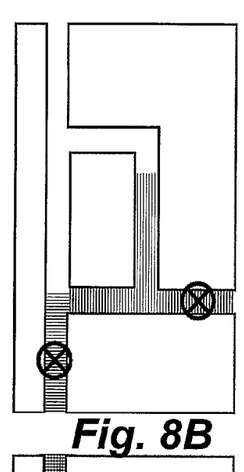
Figure 8C:
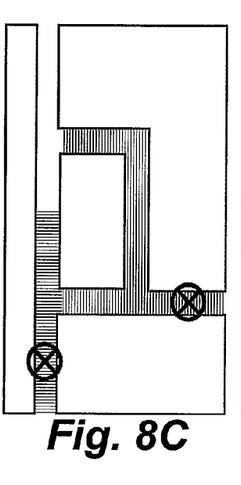
Figure 8D:
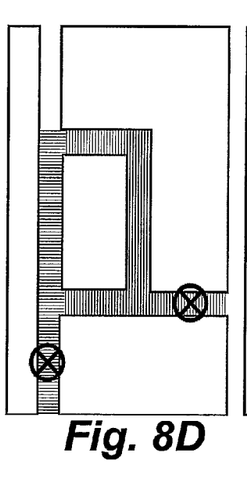
Figure 8E:
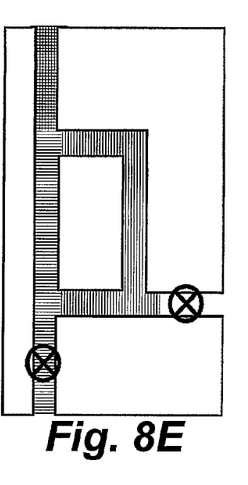
Figure 8F:
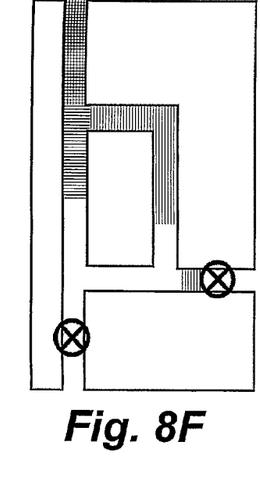
Figure 8G:
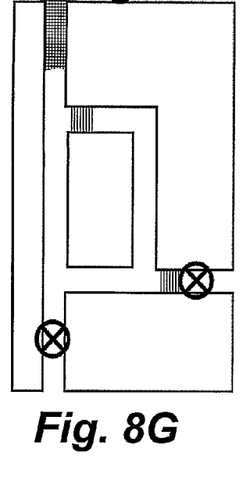

FIGS. 8A through 8G illustrate top views of a third embodiment of the invention. This embodiment is similar to the second embodiment, described immediately above, except that two sensors are used: a first one in the horizontal tributary channel, and a second one in the vertical tributary channel. According to this embodiment, a first sensor detects the arrival of the first fluid (FIG. 8A) and shuts down the pressure driving the first fluid until the second sensor detects the arrival of the second fluid (FIG. 8B). At that time drive pressure resumes for the first fluid (FIG. 8C). Thereafter, both fluids proceed through their respective channels to the mixing junction (FIG. 8D). Mixing proceeds until the first sensor detects the end of the first tributary fluid's supply (FIG. 8E) and the second sensor detects the end of the second tributary's fluid supply (FIG. 8F). Subsequently the second tributary driving pressure is maintained for an interval so that all of the second tributary fluid remaining in the apparatus is mixed (FIG. 8G). Note that in FIG. 8G, all of the second tributary fluid is mixed, although a small amount of first tributary fluid is left unmixed in the apparatus. A purpose and a benefit of using two sensors in FIG. 8A-8G is that now both of the working fluids and their respective trailing boundaries may arrive at the double merging structure in arbitrary orders of time. This makes the fluidic control much more flexible and robust. FIG. 8A-8G just show one of several possible scenarios for creating a continuous downstream flow.

Figures 9A, 9B:
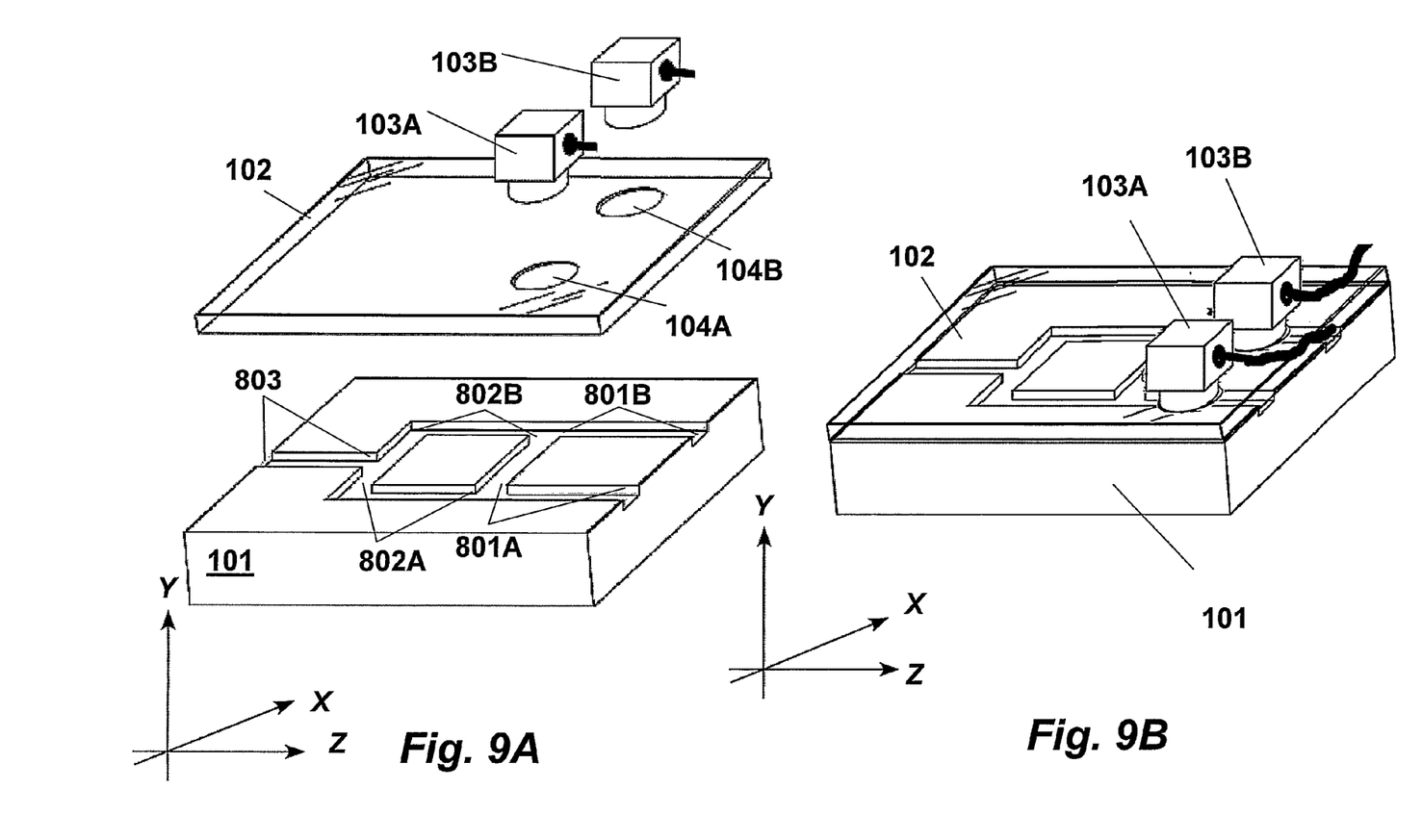
FIGS. 9A and 9B respectively provided exploded and assembled views according to a third embodiment of the invention.
Figure 10A:
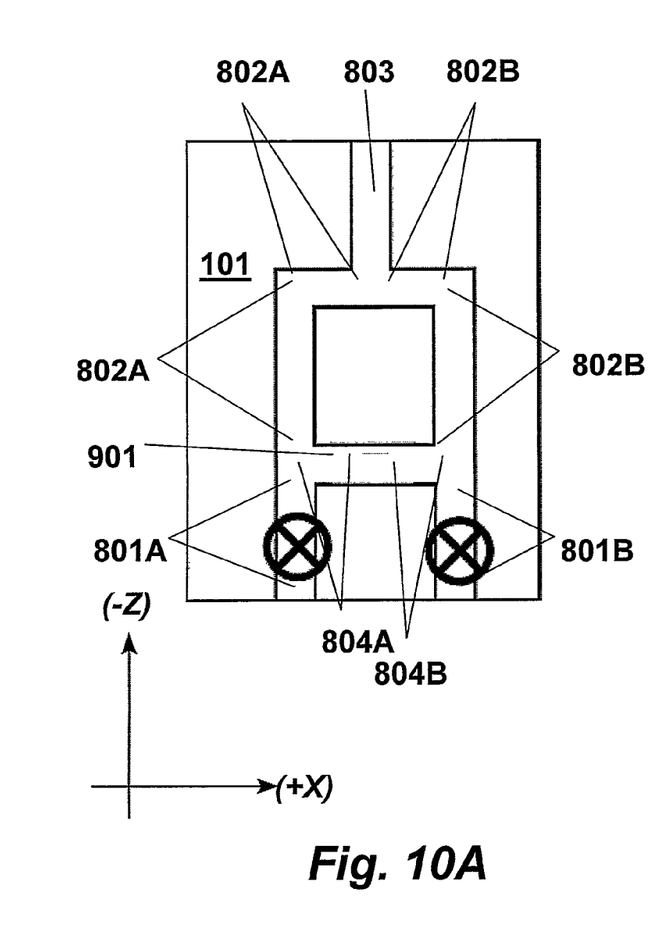
FIG. 10A illustrates a top view of the third embodiment of the invention.

FIGS. 9A and 9B respectively provided exploded and assembled views according to a third embodiment of the invention. FIG. 10A provides a top view of the third embodiment. According to this embodiment, first and second working fluid tributary channels 801A and 801B are handled in a symmetrical fashion for fluid stream merging. According to this embodiment, there are two fluid sensors, 103A and 103, one for each respective tributary channel. The structure is largely analogous to the non symmetric case, discussed above in relation to Figures five through eight. In the symmetric embodiment, the 804A/804B junction corresponds to the second junction (501/502) of the non symmetric embodiment. The 801A/804A and 801B/804B junctions correspond to the first, branching junction (501/504). (Note that in this embodiment, the introduction of the 801B/804B junction for the second working fluid renders the fluid flow paths for the first and second working fluids symmetrical.) The 802A/803/802B junction corresponds to the third, mixing junction (503/504/505). FIGS. 11A through 11H illustrate top views of an operation of the third embodiment that is analogous to the operation described for the third embodiment in connection with FIG. 8, above.

Figure 10B:
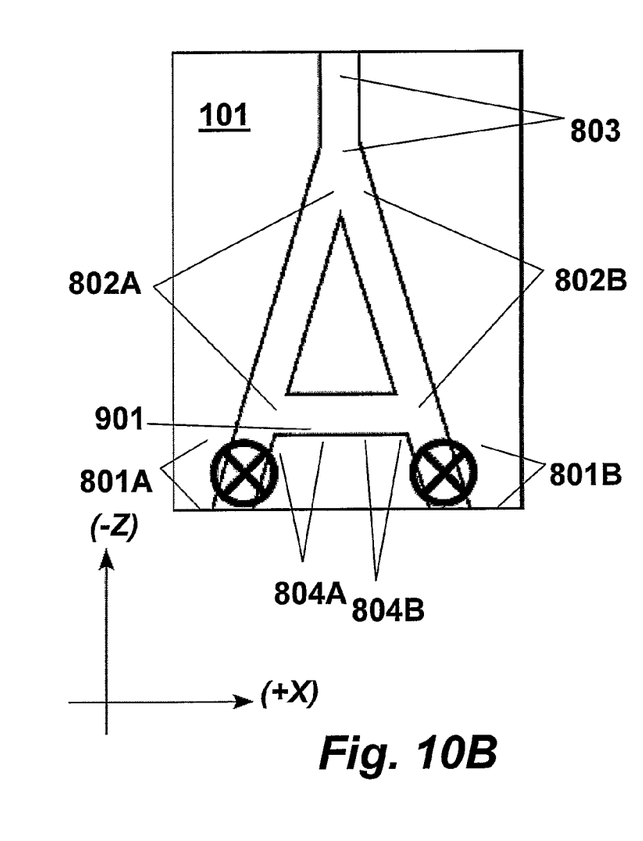
FIG. 10B illustrates a top view of an alternate version of the third embodiment of the invention.
Figure 11A:
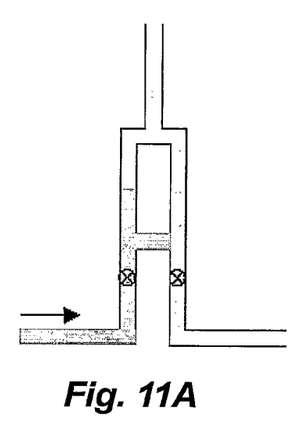
FIGS. 11A through 11H illustrate top views of an operation of the second embodiment of the invention.
Figure 11B:
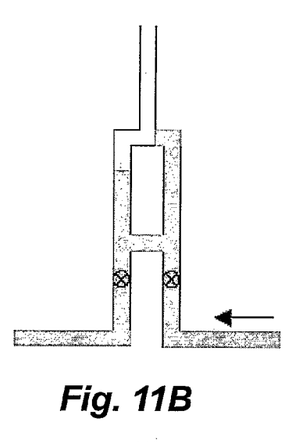
Figure 11C:
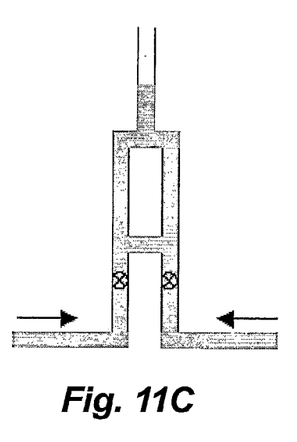
Figure 11D:
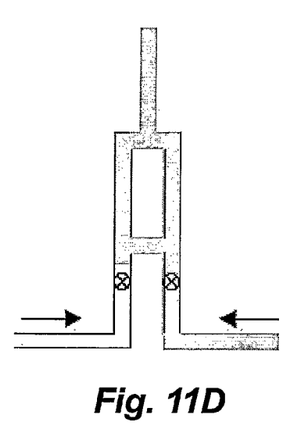
Figure 11E:
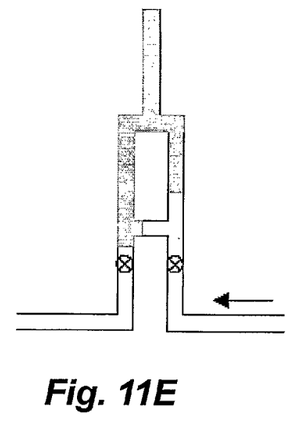
Figure 11F:
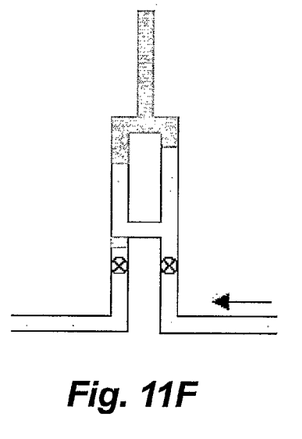
Figure 11G:
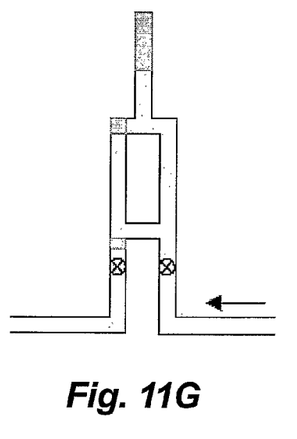
Figure 11H:
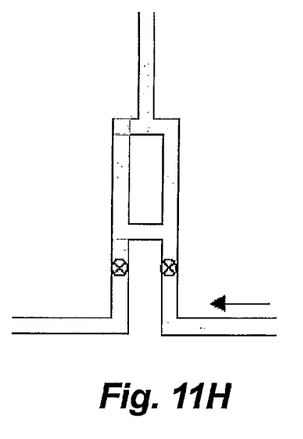

FIG. 10B illustrates a top view of an alternate layout of the third embodiment in which the elbows of the 802A and 902B channels of FIG. 10A have been eliminated, to reduce fluid flow resistance.

Figure 12:
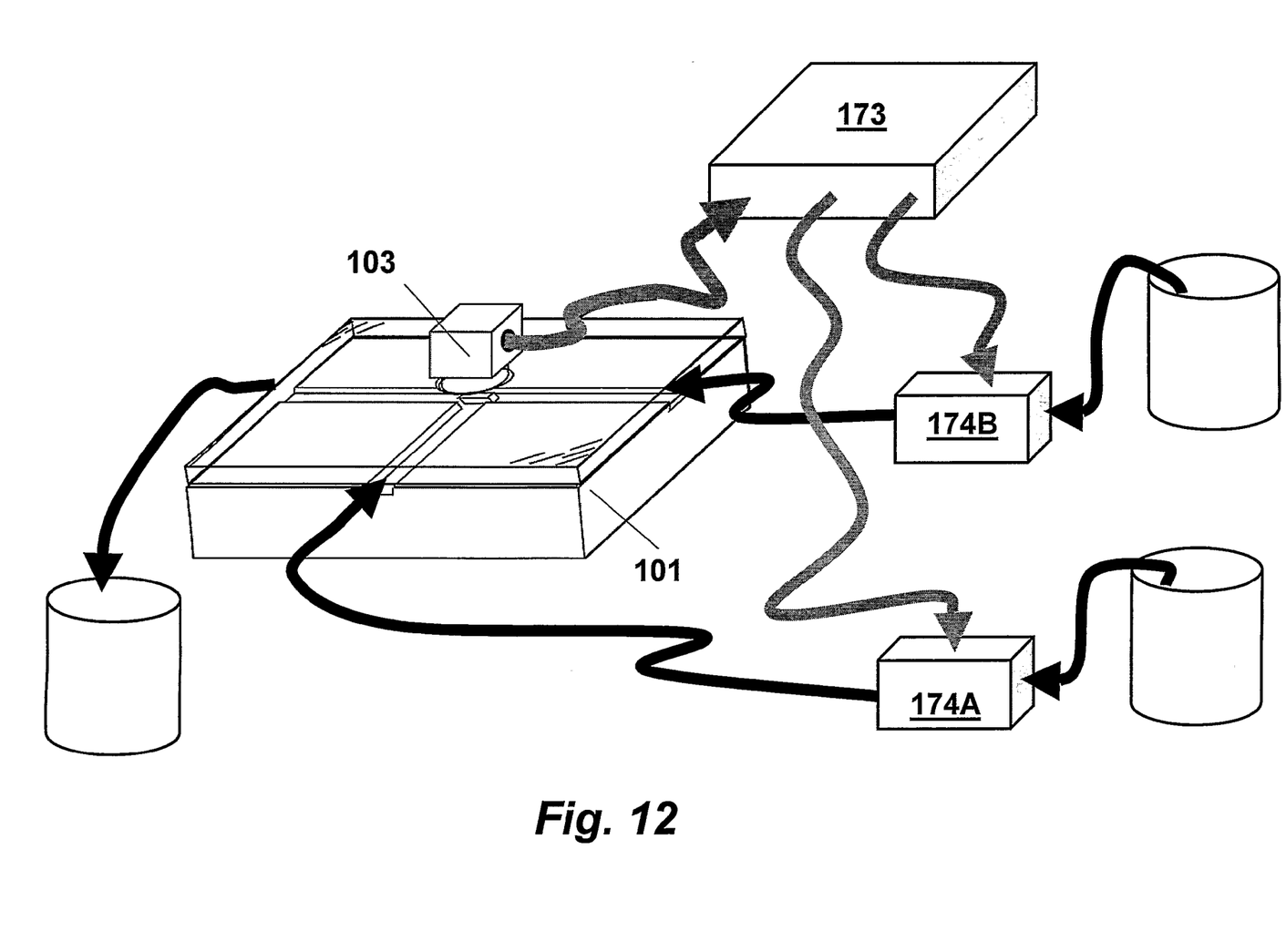
FIG. 12 illustrates a system comprising embodiments of the invention.

FIG. 12 illustrates a system comprising the above described embodiments in which a junction sensor 103 is operably coupled to a controller 173 that activates pressure pumps 174A and 174B that drive their respective working fluid tributary flows. For the embodiments described above, a first sensor signal, corresponding to the arrival of a first working fluid flow front would generally trigger a reduction in pressure by a pump driving the flow of the first working fluid. A second sensor signal, corresponding to the arrival of a second working fluid flow front would indicate the both working fluids were present at an junction and ready for merging, generally triggering a resumption in pressure by the pump driving the flow of the first working fluid. Through sensor signal magnitude analysis by the controller, the simultaneous arrival of both first and second working fluid flow fronts can be detected, in which case a change in pump pressure would not be made.

It should be understood that the invention can be practiced with modification and alteration within the spirit and scope of the appended claims. The description is not intended to be exhaustive or to limit the invention to the precise form disclosed, nor to limit the invention to the exemplary uses described. For example, the above embodiments have in some cases described a sequencing of events with respect to first and second working fluid flows. This sequencing can be reversed, or actually be made simultaneous for the fluid flows without impacting the operation of the embodiments. Also, all of the above embodiments describe the merging of two fluid flow streams. The merging of three or more fluid flow streams would be readily apparent to one of ordinary skill in the arts after reading the description, above. It should therefore be understood that the invention can be practiced with modification and alteration and that the invention be limited only by the claims and the equivalents thereof.

The invention claimed is:

1. A microfluidic flow merging apparatus comprising:
   first and second tributary channels;
   an effluent channel;
   a junction formed at the joining of the first and second tributary channels, and the effluent channel;
   a flow obstruction formed within the junction;
   at least one fluid sensor configured proximate to the junction to sense the presence of working fluids;
   a pressure pump configured to drive a working fluid flow in one of the tributary channels; and
   a controller configured to be in operable communication with the fluid sensor and the pressure pump,
   wherein the first and second tributary channels, the effluent channel, the junction, and the flow obstruction are formed by walls comprising a hydrophilic material, and wherein the controller is configured to control the pressure pump responsive to a signal from the fluid sensor.

2. The microfluidic flow merging apparatus of claim 1, wherein the controller is configured to reduce a working fluid drive pressure from the pressure pump responsive to a first signal from the fluid sensor, and to restore the working fluid drive pressure responsive to a second signal from the fluid sensor.

3. A microfluidic flow merging apparatus comprising:
   a first tributary channel;
   a branching channel, joined to the first tributary channel at a first junction;
   a second tributary channel joined to the first tributary channel at a second junction;
   an intermediate effluent channel joined to the first tributary channel and the second tributary channel at the second junction;
   an effluent channel, joined to the intermediate effluent channel and the branching channel at a third junction but not jointed to the first tributary channel or the second tributary channel;
   at least one fluid sensor configured proximate to the second junction to sense the presence of working fluids;
   a pressure pump configured to drive a working fluid flow in one of the tributary channels; and a controller configured to be in operable communication with the fluid sensor and the pressure pump, wherein the first and second tributary channels, the branching channel, the intermediate effluent channel, the effluent channel, the first, second and third junctions, are formed by walls comprising a hydrophilic material, and wherein the controller is configured to control the pressure pump responsive to a signal from the fluid sensor.

4. The microfluidic flow merging apparatus of claim 3, further comprising a flow obstruction formed in the second junction.

5. The microfluidic flow merging apparatus of claim 3, wherein the controller is configured to reduce a working fluid drive pressure from the pressure pump responsive to a first signal from the fluid sensor, and to restore the working fluid drive pressure responsive to a second signal from the fluid sensor.

6. A microfluidic flow merging apparatus comprising:
a first tributary channel;
a first intermediate tributary channel
a first branching channel, joined to the first tributary channel and the first intermediate tributary channel at a first junction;
a second tributary channel;
a second intermediate tributary channel;
a second branching channel, joined to the second tributary channel and the second intermediate tributary channel at a second junction;
a third junction joining the first and second branching channels;
an effluent channel;
a fourth junction joining the first intermediate tributary channel, the second intermediate tributary channel, and the effluent channel;
first and second fluid sensors configured proximate to the first and second tributary channels, respectively, to sense the presence of working fluids;
a pressure pump configured to drive a working fluid flow in one of the tributary channels; and
a controller configured to be in operable communication with the fluid sensor and the pressure pump,
wherein the first and second tributary channels, the first and second branching channels, the first and second intermediate tributary channels, the intermediate effluent channel, the effluent channel, and the first, second, third and fourth junctions, are formed by walls comprising a hydrophilic material, and wherein the controller is configured to control the pressure pump responsive to a signal from at least one of the first and second fluid sensors.

7. The microfluidic flow merging apparatus of claim 6, further comprising a flow obstruction formed in the second junction.

8. The microfluidic flow merging apparatus of claim 6, wherein the controller is configured to reduce a working fluid drive pressure from the pressure pump responsive to a first signal from the first fluid sensor, and to restore the working fluid drive pressure responsive to a second signal from the second fluid sensor.

* * * * *